US011443832B2

(12) United States Patent
Israeli et al.

(10) Patent No.: US 11,443,832 B2
(45) Date of Patent: Sep. 13, 2022

(54) GENETIC MUTATION DETECTION USING DEEP LEARNING

(71) Applicant: NVIDIA Corporation, Santa Clara, CA (US)

(72) Inventors: Johnny Israeli, San Jose, CA (US); Avantika Lal, Burlingame, CA (US); Michael Vella, Princes Risborough (GB); Nikolai Yakovenko, Palo Alto, CA (US); Zhen Hu, Redwood City, CA (US)

(73) Assignee: NVIDIA Corporation, San Jose, CA (US)

( * ) Notice: Subject to any disclaimer, the term of this patent is extended or adjusted under 35 U.S.C. 154(b) by 860 days.

(21) Appl. No.: 16/296,135

(22) Filed: Mar. 7, 2019

(65) Prior Publication Data

US 2020/0286587 A1    Sep. 10, 2020

(51) Int. Cl.
*G16B 30/00* (2019.01)
*G06K 9/62* (2022.01)
*G06N 3/04* (2006.01)
*G06N 3/08* (2006.01)

(52) U.S. Cl.
CPC ........... *G16B 30/00* (2019.02); *G06K 9/6256* (2013.01); *G06K 9/6267* (2013.01); *G06N 3/0418* (2013.01); *G06N 3/08* (2013.01)

(58) Field of Classification Search
None
See application file for complete search history.

(56) References Cited

U.S. PATENT DOCUMENTS

| 9,922,285 | B1 | 3/2018 | Glode et al. | |
| 2016/0283654 | A1 | 9/2016 | Ye et al. | |
| 2016/0283655 | A1 | 9/2016 | Ye et al. | |
| 2017/0249547 | A1 | 8/2017 | Shrikumar et al. | |
| 2019/0114544 | A1* | 4/2019 | Sundaram | G16H 70/60 |
| 2020/0342955 | A1* | 10/2020 | Guo | G16H 50/30 |
| 2021/0257050 | A1* | 8/2021 | Lam | G16B 40/20 |

FOREIGN PATENT DOCUMENTS

| CA | 2894317 A | 12/2016 |
| WO | 2016201564 A1 | 12/2016 |

(Continued)

OTHER PUBLICATIONS

Poplin et al ("Creating a universal SNP and small indel variant caller with deep neural networks", bioRxiv, Mar. 20, 2018 (Mar. 20, 2018), XP055585250, DOI: 10:1101/092890, pp. 1-24, https://www.biorxiv.org/content/biorxiv/early/2018/03/20/092890.full.pdf) (Year: 2018).*

(Continued)

*Primary Examiner* — Leon Viet Q Nguyen
(74) *Attorney, Agent, or Firm* — FisherBroyles LLP; Adam K. Whiting

(57) ABSTRACT

The present disclosure provides methods, systems, and computer program products that use deep learning models to classify candidate mutations detected in sequencing data, particularly suboptimal sequencing data. The methods, systems, and programs provide for increased efficiency, accuracy, and speed in identifying mutations from a wide range of sequencing data.

15 Claims, 8 Drawing Sheets

(56) References Cited

FOREIGN PATENT DOCUMENTS

| WO | 2018006152 A1 | 1/2018 |
|---|---|---|
| WO | 2018094360 A2 | 5/2018 |

OTHER PUBLICATIONS

PCT/US2020/021229, International Search Report and Written Opinion of the International Searching Authority, dated Jun. 18, 2020.
Nielsen et al., "Genotype and SNP calling from next-generation sequencing data," Nat Rev. Genet. Jun. 2011; 12(6): 443 451.
Freed et al., "The Sentieon Genomics Tools—A fast and accurate solution to variant calling from next-generation sequence data," bioRxiv preprint first posted online Mar. 10, 2017; doi: http://dx.doi.org/10.1101/115717.
Goodwin et al., "Coming of age: ten years of next-generation sequencing technologies," Nature Reviews Genetics, vol. 17:333-351 (Jun. 2016).
Hiranuma et al., "DeepATAC: A deep-learning method to predict regulatory factor binding activity from ATAC-seq signals," bioRxiv preprint first posted online Aug. 6, 2017; doi: http://dx.doi.org/10.1101/172767.
Israeli, "Deep Learning for Shallow Sequencing," presented at GTC Silicon Valley, Session S8602, Mar. 2018.
Kelley et al., "Basset: learning the regulatory code of the accessible genome with deep convolutional neural networks," Genome Res. 2015 26:990-999.
Koh et al., "Denoising genome-wide histone ChIP-seq with convolutional neural networks," Bioinformatics, 33, 2017, i225-i233; doi: 10.1093/bioinformatics/btx243.
Poplin et al., "Creating a universal SNP and small indel variant caller with deep neural networks," bioRxiv preprint first posted online Dec. 14, 2016; doi: http://dx doi.org/10.1101/092890.
Schep et al., "chromVARar: inferring transcription-factor-associated accessibility from single-cell epigenomic data," Nature Methods, published online 21 2017; doi:10.1038/nmeth.4401.
Thibodeau et al., "A neural network based model effectively predicts enhancers from clinical ATAC-seq samples," www.nature.com/ScientificReports (2018) 8:16048 | DOI:10.1038/s41598-018-34420-9; published online: Oct. 30, 2018.
Vaswani et al., "Attention Is All You Need," arXiv:1706.03762v5 [cs.CL] Dec. 6, 2017; 31st Conference on Neural Information Processing Systems (NIPS 2017), Long Beach, CA, USA.
Zhou et al., "Predicting effects of noncoding variants with deep learning-based sequence model," Nature Methods, 12 (10): 931-934; published online Aug. 24, 2015; doi:10.1038/nmeth.3547.
Li et al., "The Sequence Alignment/Map format and SAMtools," Bioinformatics 25(16): 2078-2079 (2009).
The SAM/BAM Format Specification Working Group, "Sequence Alignment/Map Format Specification," version c0358f5, dated Jan. 30, 2019, available online at https://github.com/samtools/hts-specs.
"The Variant Call Format (VCF) Version 4.2 Specification," version f305206, dated Sep. 22, 2018, available online at https://github.com/samtools/hts-specs.

* cited by examiner

FIG. 6
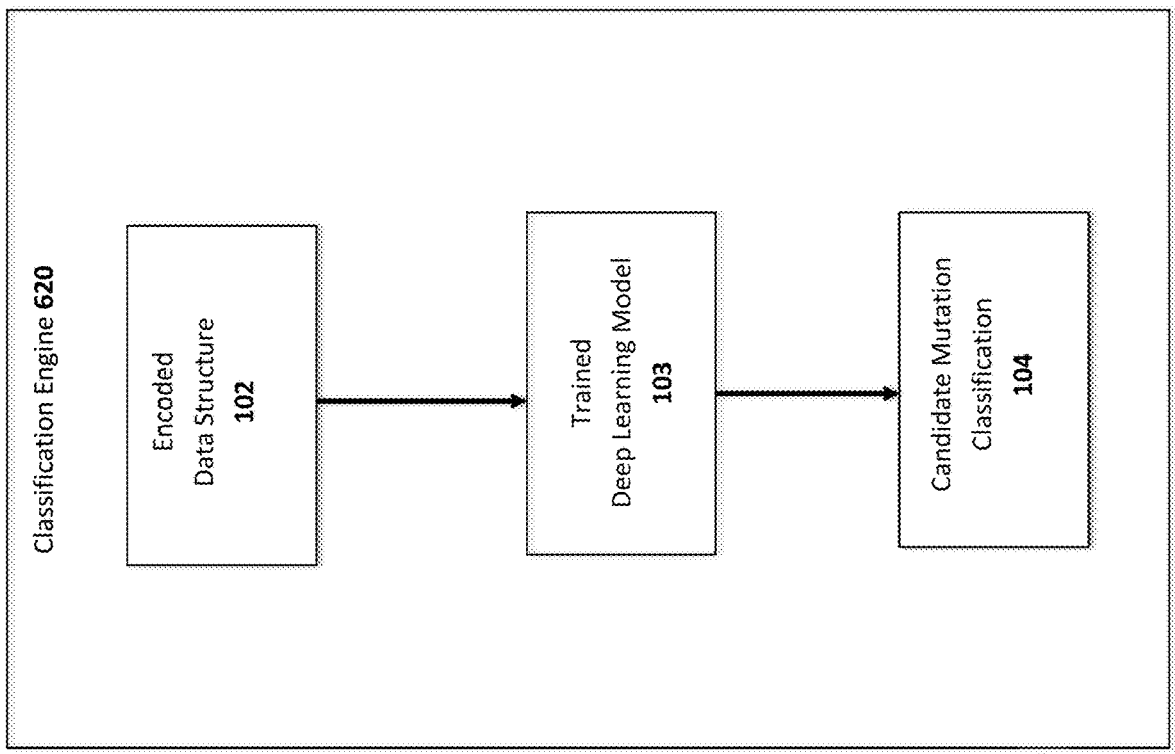
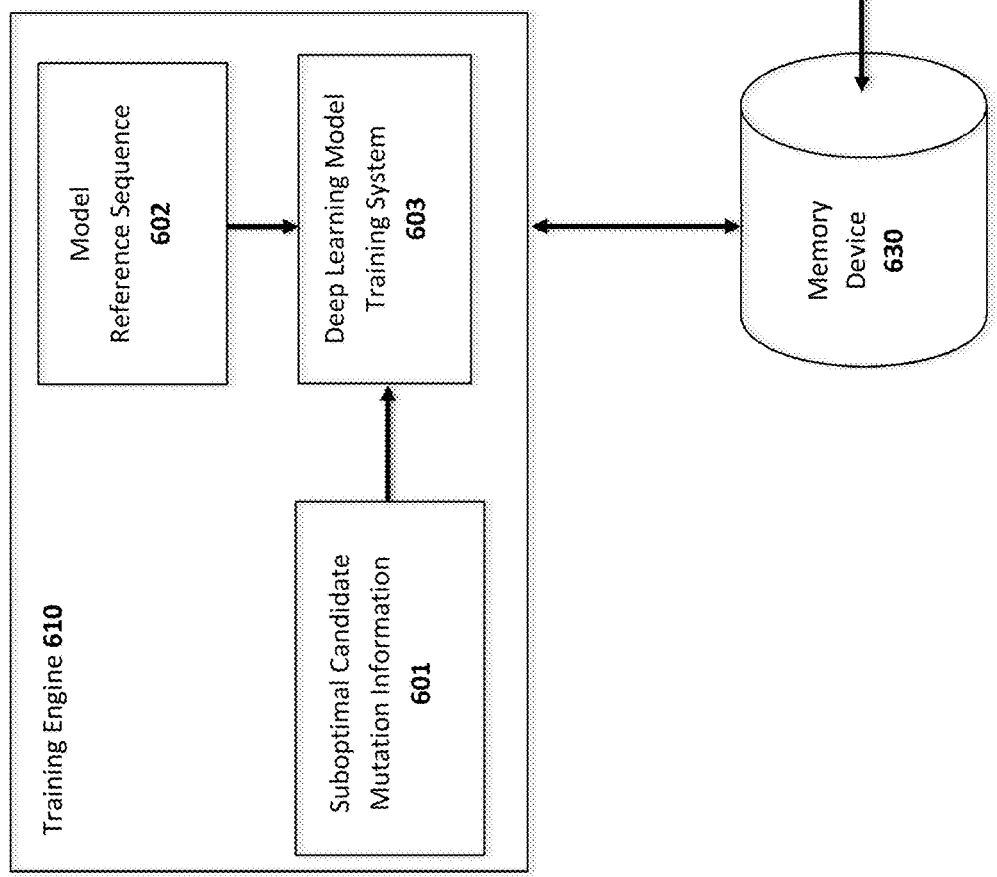

GENETIC MUTATION DETECTION USING DEEP LEARNING

FIELD OF THE INVENTION

The present disclosure relates generally to methods and systems for using deep learning to detect mutations in low coverage sequencing data.

BACKGROUND OF THE INVENTION

The human genome is the complete set of nucleic acid sequences for humans, encoded as DNA within the 23 chromosome pairs in cell nuclei and in a small DNA molecule found within individual mitochondria. The human genome consists of 6 billion base pairs that include both protein-coding DNA genes and noncoding DNA. The Human Genome Project published the first complete sequence of an individual human genome in 2001. Currently, thousands of human genomes have been completely sequenced, and many more have been mapped at lower levels of resolution. The resulting data are used worldwide in biomedical science, anthropology, forensics, and other branches of science. There is a widely held expectation that genomic studies will lead to advances in the diagnosis and treatment of diseases, and to new insights in many fields of biology, including human evolution.

Understanding the genetic basis of disease, however, requires that genomic DNA sequences of individuals are accurately and rapidly determined down to the single base pair level. This level of resolution in DNA sequencing allows the identification of natural variation in sequences that occurs between different individuals. These individual sites of sequence variation, commonly referred to as a single nucleotide variation (SNV) or single nucleotide polymorphism (SNP), exist throughout individual genomes and provide potentially critical to the use of genomic sequence information across the full range of applications. SNP refers to a variation in a position of a genome sequence that occurs in different human population. For example, at a specific human genomic position the nucleotide C may appear in most humans, but in a minority of individuals an A may occur at the same genomic position. These two different nucleotides are referred to as alleles for the particular position of the genome. It is estimated that a SNP occurs on average every 300 bp across the human genome resulting in the average human genomic sequence having approximately 10 million SNPs relative to a reference genome.

SNPs generally refer to variants found in the genome of human germline cells. SNV is a more general term and can include the variation of a single nucleotide at a specific site that may occur in a somatic cell genome. Cancer cells represent a highly studied class of somatic cells that include SNVs that are believed to be critical to their pathological phenotype and diagnosis.

DNA sequencing technology has advanced greatly since the first determination of an individual human genome in 2000 which was estimated to have cost $2.7 billion. Currently, the most advanced high-throughput techniques, commonly referred to as "next generation sequencing" (NGS). NGS technologies have enabled large scale sequencing of the genomes of plants and animals and made the process of determining a whole genome sequence achievable in as little as a week for a cost of ~$1000.

NGS technologies generally work by simultaneously carrying out millions of individual overlapping sequence reaction that each generate a short sequence or "read" of a few hundred base pairs in length. Determining the sequence requires multiple sequence reads covering each base position, and typically, it is desirable to have 30-fold redundancy of reads at each base position (i.e., "30X coverage"). Accordingly, NGS generates large dataset composed of vast numbers of sequence reads. The sequence reads provided by NGS technologies, however, have relatively high error rates of ~0.1-10%. Processing of NGS thus requires highly-involved statistical error analysis for each sample. The complexity of post-reaction processing of NGS sequence reads to account for and minimize errors creates great difficulties for the process of correctly identifying or "calling" the mutations or variants in a genome sequence.

The desire to distinguish true mutations from the errors present in NGS datasets has led to the development of methods and software tools for this purpose. Two widely used software tools for used calling mutations, such as SNPs, SNVs, insertions, and deletions, from NGS datasets are the Genome Analysis ToolKit or "GATK" (available at: software.broadinstitute.org/gatk/) and SAMtools (Li et al., "The Sequence Alignment/Map format and SAMtools," Bioinformatics 25(16): 2078-2079 (2009)). These widely-used mutation calling software tools use "classical" methods for aligning sequence reads, and bioinformatic analysis and machine-learning modeling of the aligned reads to call the mutations. The "classical" bioinformatic and machine learning components of these software tools require labor-intensive "hand-crafting" of data features, which greatly limits their ability to generalize across sequencing datasets obtained from different types of sequencing machines and/or data having different depths of coverage. Moreover, the mutation calling accuracy of the classical tools, such as GATK, deteriorates significantly when applied to sequencing datasets that are suboptimal (e.g., low coverage).

DeepVariant is a deep learning-based software tool developed to improve upon the classical mutation calling tools (see e.g., Poplin et al., "Creating a universal SNP and small indel variant caller with deep neural networks," bioRxiv 092890; doi: doi.org/10.1101/092890; published Dec. 14, 2016). DeepVariant uses a convolutional neural network (CNN) to call genetic variation in aligned NGS read data by learning statistical relationships between images of read pileups around putative variants sites and ground-truth genotype calls. DeepVariant has been shown to outperform GATK on benchmark whole genomes with 30X sequencing depth and generalize better to data from sequencing machines that had not been used during training. The accuracy of DeepVariant for calling variants using low-coverage sequencing data is unclear.

Thus, there remains a need for improved methods that decrease the cost, processing time, and sample requirements for high accuracy mutation detection from sequencing data.

SUMMARY OF THE INVENTION

The present disclosure provides methods, systems, and computer program products that use deep learning models to classify candidate mutations detected from high-throughput nucleic acid sequencing data. The methods, systems, and programs provide for increased efficiency, accuracy, and speed in classifying candidate mutations (e.g., calling SNPs) detected in sequencing data from a range of sequencing machines. It is a surprising result of the present disclosure that by extracting and encoding select information representing candidate mutations (e.g., information from SAMtools or GATK software tools), encoding that select information in a data structure that associates a copy of the reference sequence with each read sequence, and processing that encoded information with a deep learning model, an accurate classification of the candidate mutation (i.e., as a true mutation or not) can be obtained, even from suboptimal (e.g., low coverage) sequencing data. The effect of this process is a significant reduction in the time and cost of sequencing germline and somatic genomes and accurately classifying the presence and identity of mutations found therein.

In some embodiments, the present disclosure provides a method comprising:

encoding information representing a candidate mutation, wherein the information comprises absolute location, reference sequence, number of reads (N), and read sequences; and processing the encoded information with a deep learning model that classifies the candidate mutation.

In some embodiments, the method is carried out wherein the encoding associates the reference sequence with each read sequence, whereby the deep learning model jointly processes the reference sequence with each read sequence. In some embodiments, the encoding augments the reference sequence, augments the read sequence, and/or aligns the augmented reference sequence with each read sequence. In some embodiments, the encoded information further comprises read mapping quality values and/or read base quality values. In some embodiments, the reference sequence and the read sequences are encoded as 2D Boolean matrices; optionally, wherein read mapping quality values and/or read base quality values are associated with the read sequence 2D Boolean matrices.

In some embodiments, the method is carried out wherein processing with a deep learning model comprises transforming the encoded information in parallel with a plurality of CNNs of different kernel sizes and combining the output into a tensor. In some embodiments, combining the output comprises generating a ranking score and using the score to generate a TopK-selected tensor. In some embodiments, the processing with a deep learning model further comprises transforming the tensor with a CNN comprising a 1D convolutional layer followed by a plurality of fully connected layers, wherein the final fully connected layer outputs the classification of the candidate mutation.

In some embodiments, the method further comprises training the deep learning model, wherein training comprises:

encoding information representing a suboptimal candidate mutation, wherein the encoded information comprises absolute location, model reference sequence, number of reads (N), and read sequences;

processing the encoded information with a deep learning model that classifies the suboptimal candidate mutation; and minimizing error in the classification of the suboptimal candidate mutation relative a ground truth candidate mutation of the model reference sequence by adjusting parameters of the deep learning model.

In some embodiments of the method that further comprise training, minimizing error in the classification is carried out using a loss function. In some embodiments, the suboptimal candidate mutation is from low-coverage sequencing data, optionally, simulated low-coverage sequencing data generated from a model sequencing dataset.

In some embodiments, the present disclosure provides a system comprising:

a processor, a memory device, and a classification engine executable on the processor according to software instructions stored in the memory device, wherein the classification engine is configured to:

encode information representing a candidate mutation, wherein the encoded information comprises absolute location, reference sequence, number of reads (N), and read sequences; and process the encoded information with a deep learning model that classifies the candidate mutation.

In some embodiments of the system, the encoded information has the reference sequence associated with each read sequence, whereby the deep learning model jointly processes the reference sequence with each read sequence. In some embodiments, the encoding augments the reference sequence, augments the read sequence, and/or aligns the augmented reference sequence with each read sequence. In some embodiments, the encoded information further comprises read mapping quality values and/or read base quality values. In some embodiments, the reference sequence and the read sequences are encoded as 2D Boolean matrices; optionally, wherein read mapping quality values and/or read base quality values are associated with the read sequence 2D Boolean matrices.

In some embodiments of the system, the deep learning model comprises transforming the encoded information in parallel with a plurality of CNNs of different kernel sizes and combining the output into a tensor. In some embodiments, combining the output comprises generating a ranking score and using the score to generate a TopK-selected tensor. In some embodiments, the processing with a deep learning model further comprises transforming the tensor with a CNN comprising a 1D convolutional layer followed by a plurality of fully connected layers, wherein the final fully connected layer outputs the classification of the candidate mutation.

In some embodiments of the system, the system further comprises a training engine executable on the processor according to software instructions stored in the memory device, wherein the training engine is configured to:

encode information representing a suboptimal candidate mutation, wherein the encoded information comprises absolute location, a model reference sequence, number of reads (N), and suboptimal read sequences;

process the encoded information with a deep learning model that classifies the suboptimal candidate mutation; and minimize error in the classification of the suboptimal candidate mutation relative a ground truth candidate mutation of the model reference sequence by adjusting parameters of the deep learning model.

In some embodiments of the system, the training engine is in communication with the classification engine.

In some embodiments, the present disclosure also provides a non-transitory computer-readable medium comprising instructions for classifying candidate mutations that, when executed by a processor, cause the processor to perform one or more steps comprising:

encoding information representing a candidate mutation, wherein the encoded information comprises absolute location, reference sequence, number of reads (N), and read sequences; and processing the encoded information with a deep learning model that classifies the candidate mutation.

In some embodiments, the non-transitory computer-readable medium further comprises instructions for training the deep learning model, wherein training comprises:

encoding information representing a suboptimal candidate mutation, wherein the encoded information comprises absolute location, model reference sequence, number of reads (N), and read sequences;

processing the encoded information with a deep learning model that classifies the suboptimal candidate mutation; and minimizing error in the classification of the suboptimal candidate mutation relative a ground truth candidate mutation of the model reference sequence by adjusting parameters of the deep learning model.

In the various embodiments of the non-transitory computer-readable medium, it is contemplated that the various features useful in the methods and systems for classifying candidate mutations described above and elsewhere herein, including the deep learning architecture features and training features, can also be features in the non-transitory computer-readable medium.

BRIEF DESCRIPTION OF THE FIGURES

FIG. 5A depicts the first neural network module comprising a plurality of parallel CNNs of differing kernel sizes whose output is combined into a single tensor. FIG. 5B depicts the second neural network module comprising a CNN and fully connected layers capable of processing the output tensor of the first module representing the processed features of the encoded information and producing an output classification of the candidate mutation.

FIG. 6 depicts a block diagram of an exemplary system useful for classifying candidate mutations identified in sequencing data using a deep learning model, as well as, training the deep learning model, in accordance with embodiments of the present disclosure.

DETAILED DESCRIPTION

Figure 1:
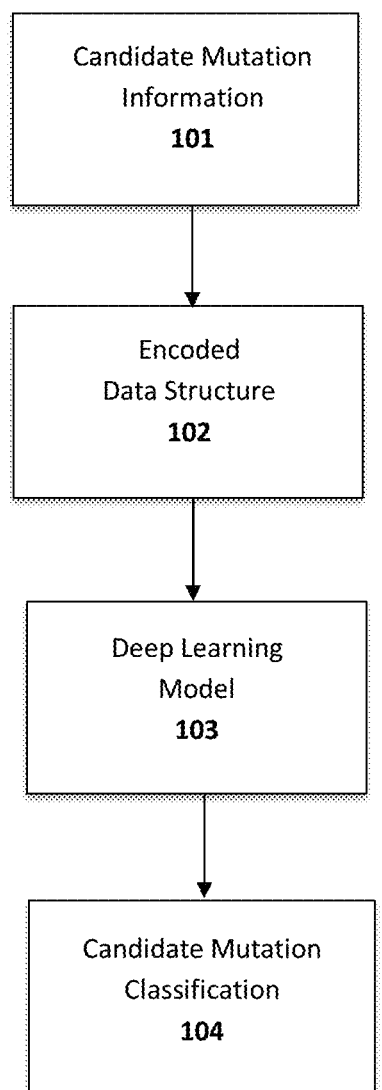
FIG. 1 depicts an overview flow diagram of exemplary operations for classifying candidate mutations identified in sequencing data in accordance with embodiments of the present disclosure.

Unless defined otherwise, all technical and scientific terms used herein have the same meaning as commonly understood by one of ordinary skill in the art to which the present invention pertains. Generally, the terms used to describe the techniques and procedures described herein are well understood and commonly employed by those of ordinary skill in the art, such as the common techniques and methodologies used for high-throughput (or next-generation) sequencing and for calling mutations (e.g., SNPs or SNVs) from this type of sequencing data. Such common techniques and methodologies for sequence data acquisition and mutation analysis are described in e.g., Goodwin et al., "Coming of age: ten years of next generation sequencing technology," Nat Rev Genet. 2016 June; 17(6):333-51; and Nielsen et al., "Genotype and SNP calling from next-generation sequencing data," Nat. Rev. Genet. 2011 June; 12(6): 443-451.

For purposes of interpreting this disclosure, where appropriate, a term used in the singular form will also include the plural form and vice versa. For the descriptions provided herein and in the appended claims, the singular forms "a", and "an" include plural referents unless the context clearly indicates otherwise. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of." Where a range of values is described, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Thus, where the stated range includes one or both of these limits, ranges excluding either or both of those included limits are also included in the invention. For example, "1 to 50," includes "2 to 25," "5 to 20," "25 to 50," "1 to 10," etc.

The ordinary artisan should appreciate that the methods, systems, and computer-readable medium products described herein provide many advantageous technical effects including improving the accuracy, speed, compactness, and overall efficiency of detecting mutations in sequencing data, even suboptimal, low-coverage data, using a deep learning model. It should also be appreciated that the following specification is not intended as an extensive overview, and as such, concepts may be simplified in the interests of clarity and brevity.

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

Use of Deep Learning to Classify Candidate Mutations

The present disclosure describes methods and systems utilizing deep learning disclosed herein may be applied to classifying mutation calls from any type of nucleic acid sequencing data. However, it is contemplated that these methods and systems will find the greatest advantage when applied to classifying candidate mutations from the massive datasets of overlapping sequence reads that are obtained from NGS experiments. A range of NGS technologies are known in the art and it is contemplated that the deep learning-based methods and systems of the present disclosure can be used to classify mutations from sequencing data obtained from any of them. For a review of NGS technologies see e.g., Goodwin et al., "Coming of age: ten years of next generation sequencing technology," Nat Rev Genet. 2016 June; 17(6):333-51.

As noted above, NGS technologies work by carrying out millions of sequencing reactions in parallel, each of which results in millions of overlapping sequences or "reads," that is typically a few hundred base pairs (bp) in length. The overlapping sequence reads results in helpful data redundancy in an NGS experiment. Currently, the standard accepted as the desired level redundancy for an accurate sequence is "30X coverage," which means that on average 30 separate sequence reads covering each base position of the sampled genome. Unfortunately, the massive number of parallel sequence reads have relatively high error rates on the order of 0.1% to 10%. Accordingly, further post-processing analysis of the errors is required to provide an accurate overall sequence for each sample. Moreover, 30X coverage is an average across the sequencing dataset. There are many locations in the dataset having far fewer (e.g., only 10) reads, and others having far more (e.g., 1000) reads. The high rate of errors in the numerous sequence reads together with the uneven level of coverage creates a particularly challenging problem when trying to use NGS sequencing data to accurately detect and confirm the presence of a mutation in a nucleic acid sequence. "Mutation" as used herein refers to any variation, change, or difference in a nucleic acid sequence relative to a reference sequence, e.g., including a single nucleotide variant (SNV), a single nucleotide polymorphism (SNP), an insertion, a deletion, or any other difference.

Typically, in high-throughput sequencing data, a difference or variation in the identity of base (e.g., A, C, G, or T) will occur in some but not all of the plurality of sequence reads that overlap or cover a specific location. These detected differences at a position in a set of sequence reads may be due to the existence of an actual mutation in the sample sequence (i.e., a true positive), or simply an error in the sequence reads due to noise or some other experimental error (i.e., a false positive). The detected but unconfirmed difference at a sequence location relative to a reference sequence is referred to as a "candidate mutation." "Candidate mutation classification" constitutes determining whether an observed mutation at a specific location relative to a reference sequence is a true mutation, and optionally, also determining the type of mutation (e.g., insertion, deletion, SNP). Up to millions of candidate mutations can be observed in a typical sequencing dataset that spans a genome ("genome" refers to a full genome, or a portion of a genome, such as an exome). The problem of classifying these numerous candidate mutations is amplified when using suboptimal sequencing datasets. "Suboptimal" refers to having a quality less than optimal. Thus, suboptimal candidate mutations would are those obtained from sequencing data of a quality less than optimal. Such data may result from any source that may be detrimental the quality of sequencing data, including the use of fewer sequencing reads (e.g., low-coverage datasets), a limited amount of sample, and/or any source capable of introducing noise or error. The ability to use suboptimal sequencing data, however, is desirable because such data can be obtained rapidly and thereby allow for faster, cheaper sequencing of the complete genomes of human individuals. Accordingly, there is much to be gained in improving methods and systems for candidate mutation classification.

The present disclosure provides methods and systems that use deep learning models to classify candidate mutation information derived from high-throughput sequencing data. In particular, the methods and systems can be used to classify candidate mutation information obtained from high-throughput sequencing datasets, including suboptimal sequencing data, such as low-coverage data obtained with less than 30X sequencing depth. By allowing accurate candidate mutation classification with low-coverage data, the deep learning-based methods and systems of the present disclosure can facilitate faster, more efficient, and more cost-effective nucleic acid sequencing resources. Faster, more efficient sequencing can thus enable wider use of nucleic acid sequencing for medical applications such as personalized medicine and diagnostics.

The deep learning models and associated techniques used in the methods of the present disclosure are based on the use of neural networks, such as convolutional neural networks (CNNs), in computer-based systems. Such deep learning models have been used successfully to extract features and classify data in a wide range of applications, most notably, image, language, and speech recognition. In order to effectively process candidate mutations derived from high-throughput sequencing datasets using a deep learning model, the appropriate sequencing data is encoded in a data structure that facilitates the use of neural networks.

FIG. 1 illustrates an overview flow diagram of the exemplary operations for classifying candidate mutations from sequencing data, particularly suboptimal sequencing data, as applied using the deep learning methods and systems described present disclosure. Candidate mutation information 101 is generated from standard sequencing data using any of the software tools well-known in the art for processing of sequencing data and making variant calls. Two of the most widely-used software tools are GATK (i.e., the "genome analysis toolkit") which is available from the Broad Institute (software.broadinstitute.org/gatk/) and SAMtools (Li et al., "The Sequence Alignment/Map format and SAMtools," Bioinformatics 25(16): 2078-2079 (2009)). These software tools carry out "classical" variant calling by aligning the numerous sequence reads from a target sample to a reference genome, and then use bioinformatic analysis and machine-learning modeling of the aligned reads to generate candidate mutations.

Candidate mutation information useful in the methods and systems of the present disclosure can be generated from standard sequencing data using standard well-known software for calling mutations. For example, a dataset of high-throughput sequence reads can be analyzed using and a corresponding reference sequence and classical variant calling software tools, such as GATK and SAMtools, to generate candidate mutations. In some embodiments, the sequencing data used in the method is a low-coverage dataset having less than an optimal number of sequence reads at each candidate mutation location. Low-coverage datasets useful in the candidate mutation classification methods of the present disclosure can include datasets having less than 30x coverage, less than 20x coverage, less than 15x coverage, or even lower coverage of the target genome sequence.

In some embodiments, the candidate mutation information 101 used in the methods and systems of the present disclosure comprises a subset of the standard information found in the file formats generated by classical variant calling software tools, such as GATK and SAMtools, such as VCF and/or BAM files. For example, candidate mutation information can be extracted from a variant call format (VCF) file. The VCF file that includes information about the specific candidate mutation position and base call, the absolute location in the genome (e.g., detailing chromosomal site), and the quality of the base call in the read sequence (BQ). The VCF file also includes a compressed sequence alignment/map format (BAM) file that contains information about the read mappings/alignments and their quality, also referred to herein as read mapping quality (MQ). The VCF and BAM file formats are well known in the art and a complete description of each is publicly available online at e.g., github.com/samtools/hts-specs.

As noted above, not all candidate mutation information generated by standard variant calling software tools is used in the deep-learning methods of the present disclosure. It is an advantage of the presently disclosed methods that selected data representing the candidate mutation information 101 is used to generate encoded information 102 that can then be processed by the deep learning model 103 to generate the output of the candidate mutation classification 104. The selection and structure of the encoded information 102 are further detailed in FIG. 2. The architecture of the deep-learning model is further detailed in FIG. 3.

Figure 2:
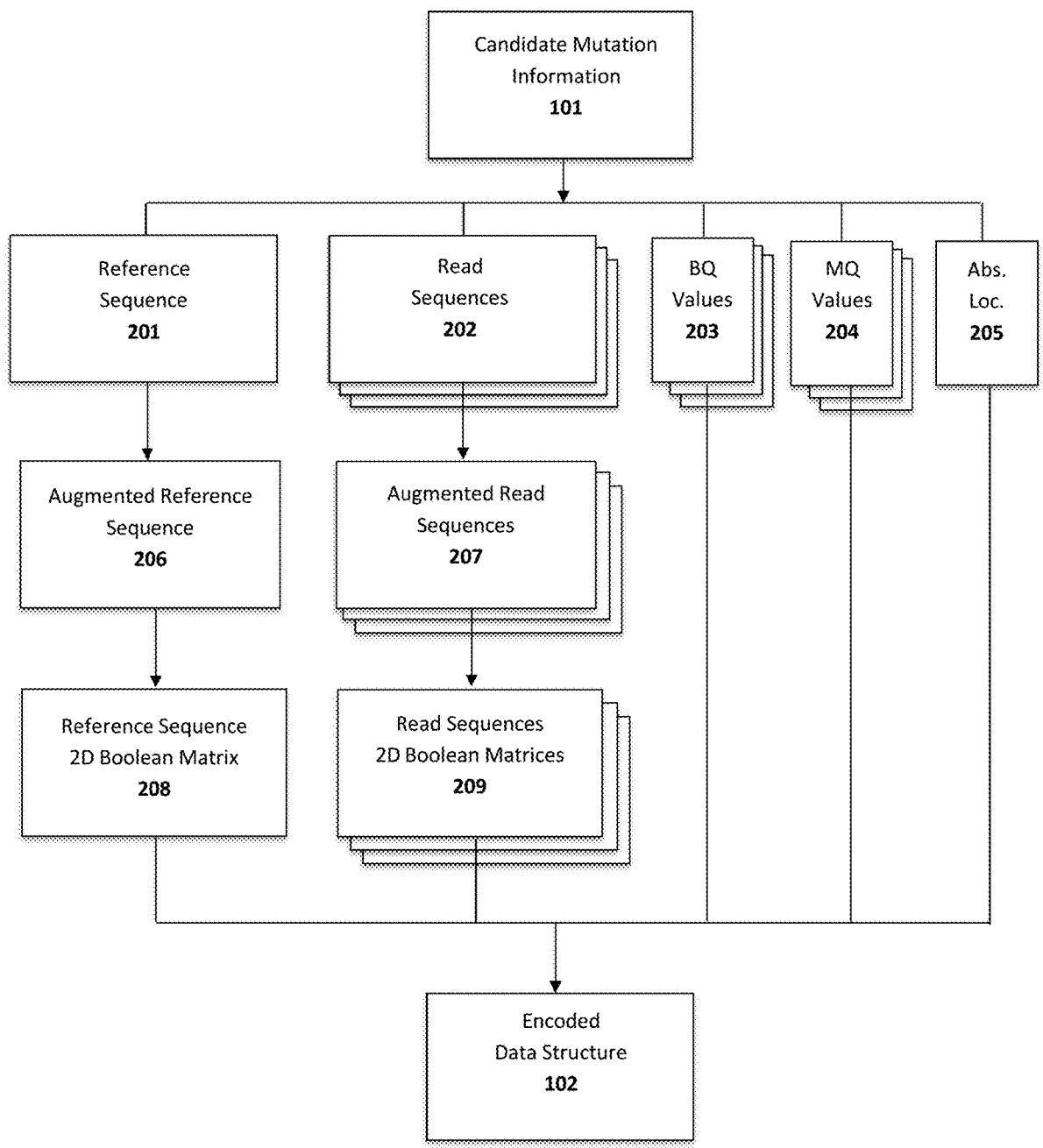
FIG. 2 depicts a block diagram of exemplary operations for use in encoding information representing candidate mutations in accordance with embodiments of the present disclosure.

FIG. 2 illustrates a block diagram of the exemplary candidate mutation information 101 that is extracted and then encoded into the data structure of the encoded information 102 such that it can be processed by a deep-learning model useful in the methods and systems of the present disclosure. In some embodiments, the information extracted and encoded includes the reference sequence 201, the read sequences 202, which includes the number N of the reads, and the absolute location 205 of the candidate mutation. The absolute location typically is represented by a numerical "address" or "index" that indicates the unambiguous site in a genome (or other reference sequence) where the candidate mutation is centered (e.g., "chromosome 1: 10009"). The set of N read sequences 202 selected are those overlapping the candidate mutation location. Similarly, the reference sequence 201 corresponds to the genome sequence that surrounds the locus of the mutation an equal distance upstream and downstream. The absolute location 205, thus defines the set of N read sequences 202 and the corresponding reference sequence 201.

The extraction and encoding of the absolute location 205, the reference sequence 201, and the N read sequences 202 constitute the basis set of candidate mutation information 101 to be included in the encoded information 102 representing the candidate mutation.

Due to the high incidence of sequencing errors (e.g., insertions and/or deletions) in NGS, the sequence reads 202 obtained from a candidate mutation generating software such as GATK frequently also misalign with the reference sequence 201. In order to encode the candidate mutation information for more accurate and efficient processing by the deep learning models, in some embodiment the encoding includes the preparation of an augmented reference sequence 206 and augmented read sequences 207. The sequences are augmented by adding insertions at positions of the reference sequence and N read sequences so as to result in an optimal alignment of the candidate mutation location and with all of the sequences having equal length. Processes and software for preparing an optimal alignment of read sequences with a reference sequence are well known in the art. The alignment process typically will result in each of the augmented read sequences 207 and/or the augmented reference sequence 206 including one or more insertions relative to the input read and reference sequences 202 and 202. The process of augmenting the sequences results in augmented reference and augmented read sequences of equal length with the sited candidate mutation site optimally aligned. This encoding of the augmented reference and read sequences further facilitates processing of the encoded information 102 by the deep learning model 103, particularly the efficiency of feature learning and extraction by the neural networks.

The reference and read sequences extracted from the candidate mutation information generated by a software tool such as GATK are represented as strings of A, C, G, and T, or integer digits representing A, C, G, and T. In order to facilitate more efficient processing by the deep learning models of the present disclosure, in some embodiments, the augmented reference and augmented read sequences are encoded as 2D Boolean matrices 208 and 209. More specifically, the Boolean matrices include five rows representing A, C, G, T, or an insertion, and a number of columns corresponding to length of the sequence with each base position represented by a column. Thus, the reference sequence and the N read sequences are represented by 2D Boolean matrices of the same dimension: five rows by sequence bp length number of columns. The presence or absence of an A, C, T, G, or insertion, at each sequence position is represented by grid of "1" or "0". Thus, each Boolean matrix column of 5 rows will include a single "1" and four "0." Such 2D Boolean matrices are rapidly and efficiently transformed by neural networks such as CNNs, greatly improving the feature learning and extraction process used in classifying the mutation candidates.

It is also contemplated that certain quality features associated with each of the N individual sequence reads, and the individual base calls in each of the reads, optionally may be included in the encoded information 102. Thus, in some embodiments, the read mapping quality score (MQ) 204, and/or the base quality scores (BQ) 203 for each base in a read can also be encoded in the encoded information along with the read sequences 202. The inclusion of the quality scores with the read sequences in the encoded information provides additional parameters useful for processing by the deep learning model 103 as described below.

Figure 3:
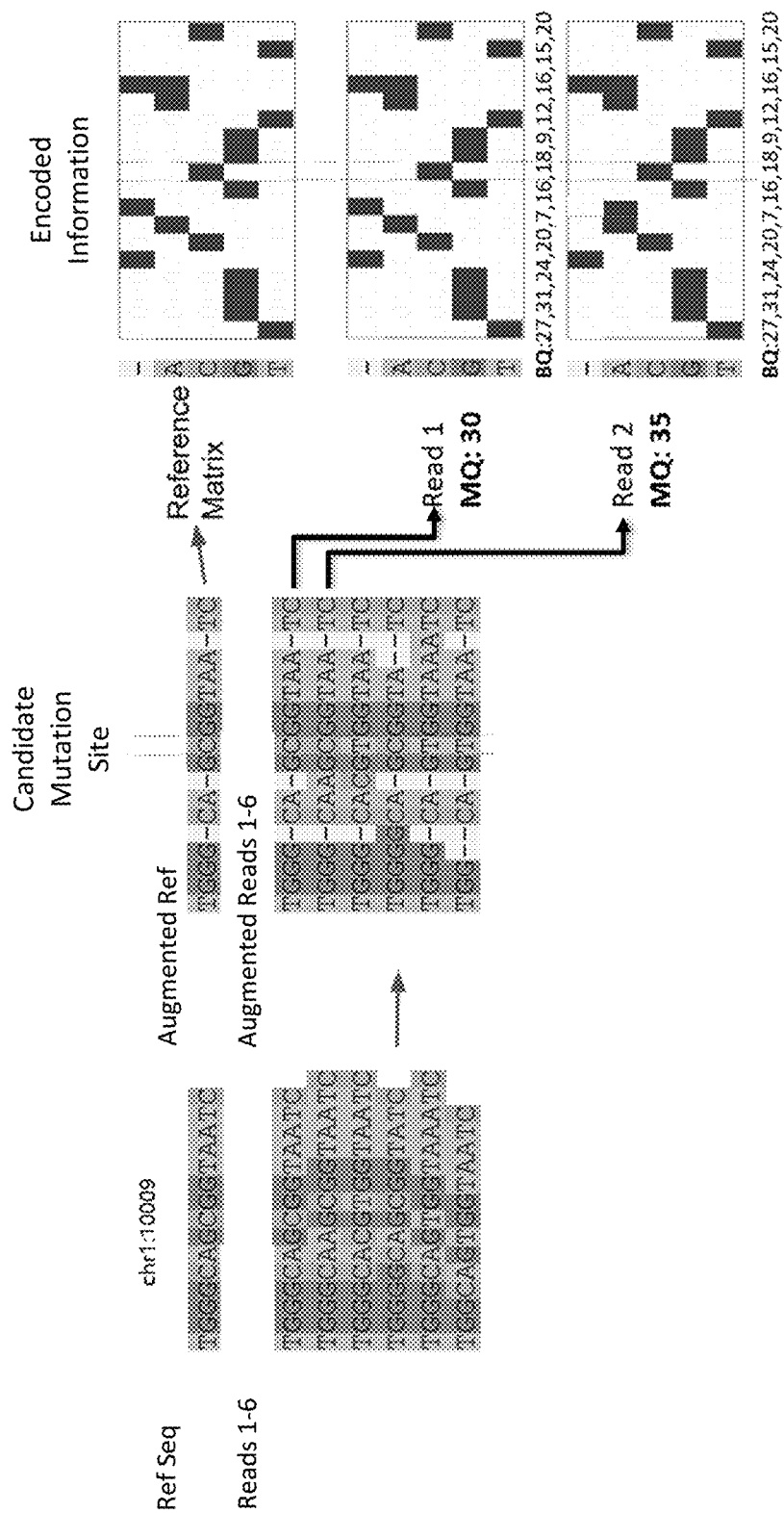
FIG. 3 depicts a schematic illustration of an exemplary process for encoding information representing an exemplary single candidate mutation.

FIG. 3 depicts a schematic illustrating an exemplary process for encoding information representing a candidate mutation. The reference sequence is a 15 bp sequence centered around a C base that is the candidate mutation site at absolute location "chr1:10009." Under the reference sequence are depicted a stack of six read sequences having from 13 to 15 bp and depending on the alignment having a C, T, or G at the candidate mutation site. The six read sequences are aligned optimally using a sequence standard alignment tool and augmented with insertion (indicated by a dash "-") so that all six are 18 bp in length with the candidate mutation site located at position 10 of the sequence. The reference sequence is also augmented with insertions and similarly aligned. In the alignment of the augmented read sequences three have a C and three have a T at the mutation site. The reference sequence has a C at the site. The augmented alignments thus illustrate the relevant mutation classification question: whether the reads indicate the presence of a T mutation at the site or whether the detected three detected T are errors or noise. In order to provide for more facile processing by a deep learning model the aligned sequences can be further encoded as 2D Boolean matrices. As shown in FIG. 3, the 2D Boolean matrices have five rows to allow for the four possible bases and the insertion at each position. The number of columns of the matrix correspond to the length (e.g., 18 bp) of each sequence. The cells of the encoded 2D matrices in FIG. 3 are depicted as either black or white but could also be represented as 1 or 0. Because the illustrated Read 1 and Read 2 differ by a base at position 8, their encoded 2D Boolean matrix patterns also differ at the cells corresponding to rows 1 and 2 of column 8. The 2D Boolean matrices for Reads 3-6 are not depicted in FIG. 3 but would have similarly distinct patterns corresponding to their distinct encoded sequence. The black and white 2D Boolean encoding of the sequences depicted in FIG. 3 highlights how this type of encoding can facilitate feature extraction processes using neural networks.

Also depicted in FIG. 3 are the read mapping quality (MQ) values for each of Read 1 (MQ: 30) and Read 2 (MQ: 35), and the read base quality (BQ) values (e.g., Read 1 BQ: 27, 31, 24, 20, 7, 16, 18, 9, 12, 16, 15, 20 . . . ). These scalar integer values can be optionally associated with the encoded 2D Boolean matrices for the read sequences. The candidate mutation information thus can be encoded to include a 2D Boolean matrix with an additional row of BQ values, and an associated MQ value. In some embodiments, each of the plurality of N read sequences encoded as a 2D Boolean matrix is associated with a copy of the corresponding augmented reference sequence which also encoded as a 2D Boolean matrix.

Figure 4:
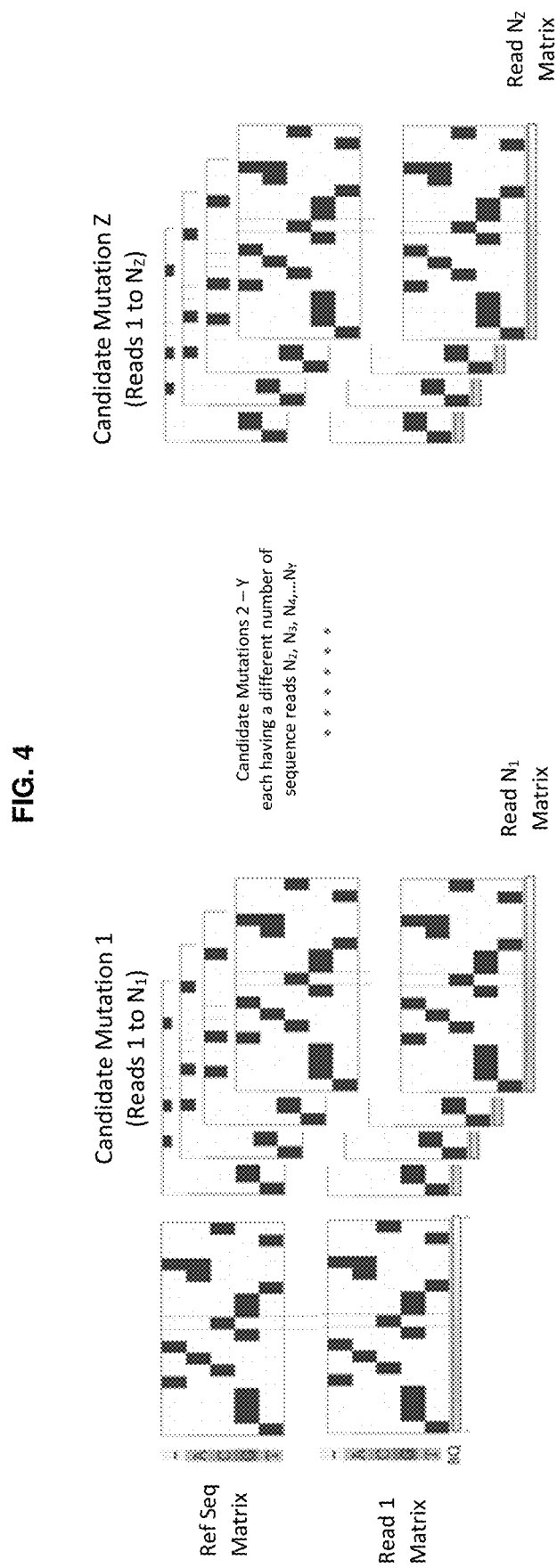
FIG. 4 depicts a schematic illustration of exemplary information encoded for an set of candidate mutations (denoted Candidate Mutation 1 through Candidate Mutation Z) obtained from a high throughput sequencing dataset.

FIG. 4 depicts a schematic illustration of exemplary information encoded for an set of candidate mutations (denoted Candidate Mutation 1 through Candidate Mutation Z) obtained from a high throughput sequencing dataset. Each candidate mutation is encoded as a set of 2D Boolean matrices corresponding to the number of sequence reads overlapping the candidate mutation location. A total of $N_1$ 2D Boolean matrices are encoded for Candidate Mutation 1, and $N_Z$ 2D Boolean matrices are encoded for Candidate Mutation Z. In this example, $N_1$ does not equal $N_Z$ and generally the number of reads N for each candidate mutation across a dataset are not the same. Each 2D Boolean matrix representing a sequence read overlapping a candidate mutation location has been augmented and associated with a copy of the reference sequence overlapping the location.

The association of the reference sequence with each individual sequence read for a candidate mutation provide a significant advantage of speed and efficiency in processing the encoded information with deep learning models as described in the methods of the present disclosure. For example, as described elsewhere herein, it provides for efficiency by allowing processing to be cut short or otherwise abbreviated for candidate mutations at locations having large numbers of redundant overlapping sequence reads.

Additionally, FIG. 4 illustrates how each 2D Boolean matrix representing a read can have the scalar BQ values for the read associated as an array of integer values (depicted as bottom row). Although not depicted in FIG. 4, representing the scalar MQ values associated with each read sequence can also be associated with each matrix.

FIG. 4 also illustrates how the 1 through N 2D matrices (each representing a difference read but each associated with a copy of the reference sequence matrix) are further assembled into a 3D matrix (i.e., a tensor) that represents all of the encoded information for the specific candidate mutation. Additionally, FIG. 4 illustrates how a large number of different candidate mutations (i.e., "Candidate Mutation 1, Candidate Mutation 2 . . . . Candidate Mutation Y, Candidate Mutation Z") that span a sequencing dataset (e.g., a covering complete genome) can be represented by a set of Z encoded 3D matrices.

It is also significant, as depicted in FIG. 4, that each of the 3D matrices can include a different number (e.g., $N_1 \ldots N_z$) of 2D Boolean matrices because in a real high throughput sequencing datasets, the number of sequence reads representing each candidate mutation can vary substantially, e.g., from N=10 to N=10,000. This inconsistency in the number of reads across the numerous candidate mutations that need to be classified across a large sequencing dataset creates difficulty in processing using neural networks. As described elsewhere herein, it is an advantage of the deep learning models of the present disclosure that such variable sized datasets are efficiently classified via the encoding of the candidate mutation information and processing in parallel with a plurality of convolutional neural network (CNN) layers of varying kernel size that combine their output in a single TopK-selected tensor.

The specific sequence data and information included and the data structure of the encoded information 102 provides advantages for use in a deep learning model for classifying candidate mutations of a genome. In particular, the encoded information associates (i.e., links) the reference sequence 201 with each of the N read sequences 202 that overlap the location of the candidate mutation. The association of the reference sequence with each of the N read sequences allows for joint processing of these by deep learning model 103. This joint processing allows for the neural networks of the model to learn and extract features in real-time, which can effectively short-cut processing of sequencing reads. For example, if a learned feature can by extracted by the neural network using only 12 of 15 read sequences, then this particular candidate mutation classification can be terminated 3 reads early and processing for the next candidate mutation begun resulting in savings of computing cost and time.

Generally, the deep learning model has an "architecture" comprising a sequence of neural networks, such as CNNs, that each includes a plurality of neural layers. The architecture can thus be described in terms of sequence of layers, the operation performed by each layer, and the connectivity between the layers. Key features of the neural network layers are the "kernels" or "filters" that perform the computational transformations on the data that is input into the layer. Each filter has an associated adjustable weighting parameter and the combination of the filters and their weights determine the exact computational transformation performed. It is the iterative adjustment of the filter weighting parameters to minimize a loss function that constitutes the "learning" during the "training" of the deep learning model. The final learned values of the weighting parameters, which are set at the end of training, determine the architecture of the deep learning model that can be used for the task of classifying candidate mutations.

As described further below, in some embodiments, the training process for the deep learning model can be abbreviated by using what is referred to as "transfer learning." Typically, transfer learning is used to train a neural network with training data that differs from the data that was originally used to originally train the neural network. Accordingly, in transfer learning the adjustments made to the weighting parameters are limited. For example, selected weights and/or selected kernels can be held constant, while others are adjusted. In this way, transfer learning can train the neural network to work better in classifying different types of datasets without carrying out a complete re-training of the neural networks.

Figure 5A:
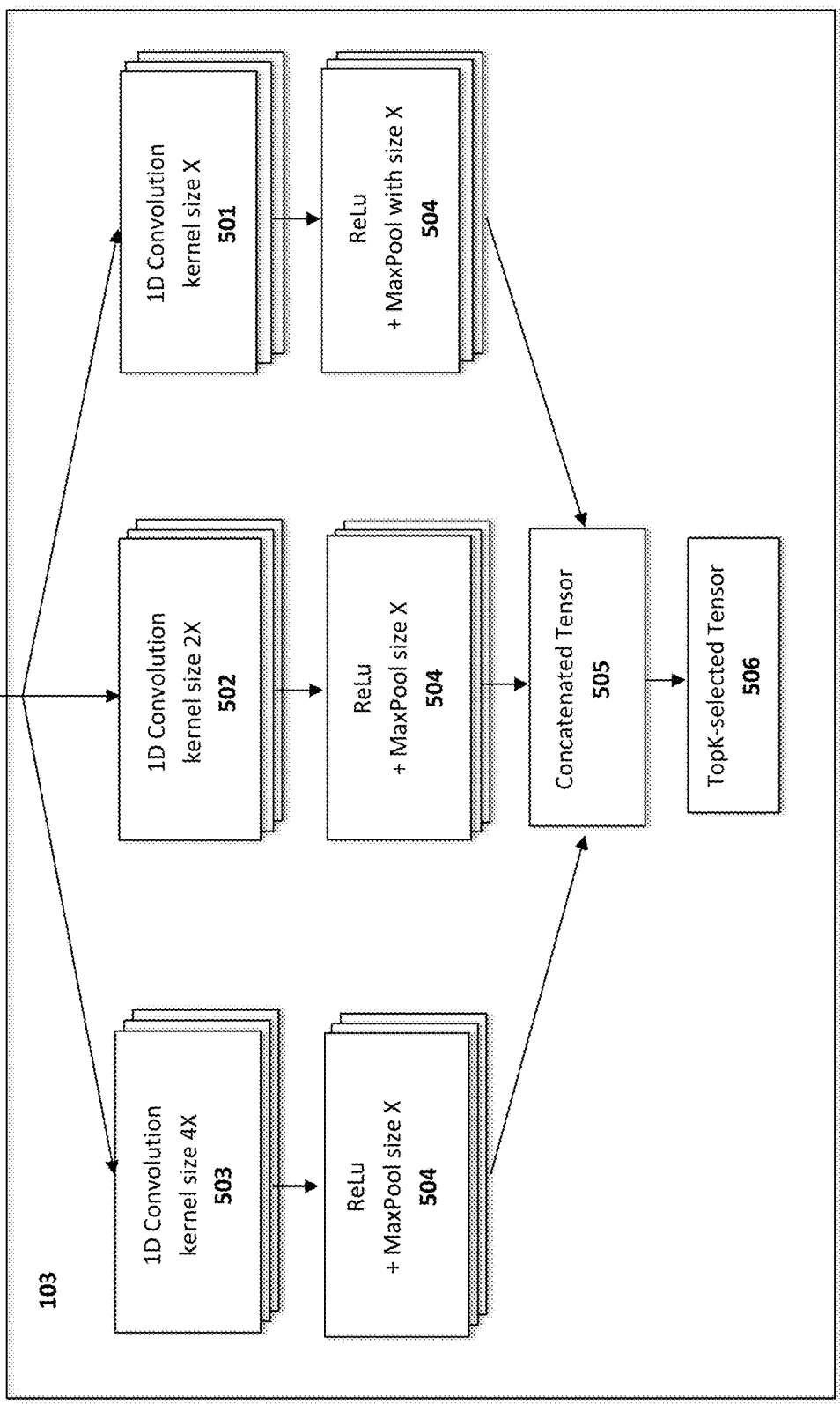
FIGS. 5A and 5B depict a block diagram of an exemplary deep learning model architecture useful for processing encoded information representing candidate mutations in accordance with embodiments of the present disclosure.
Figure 5B:
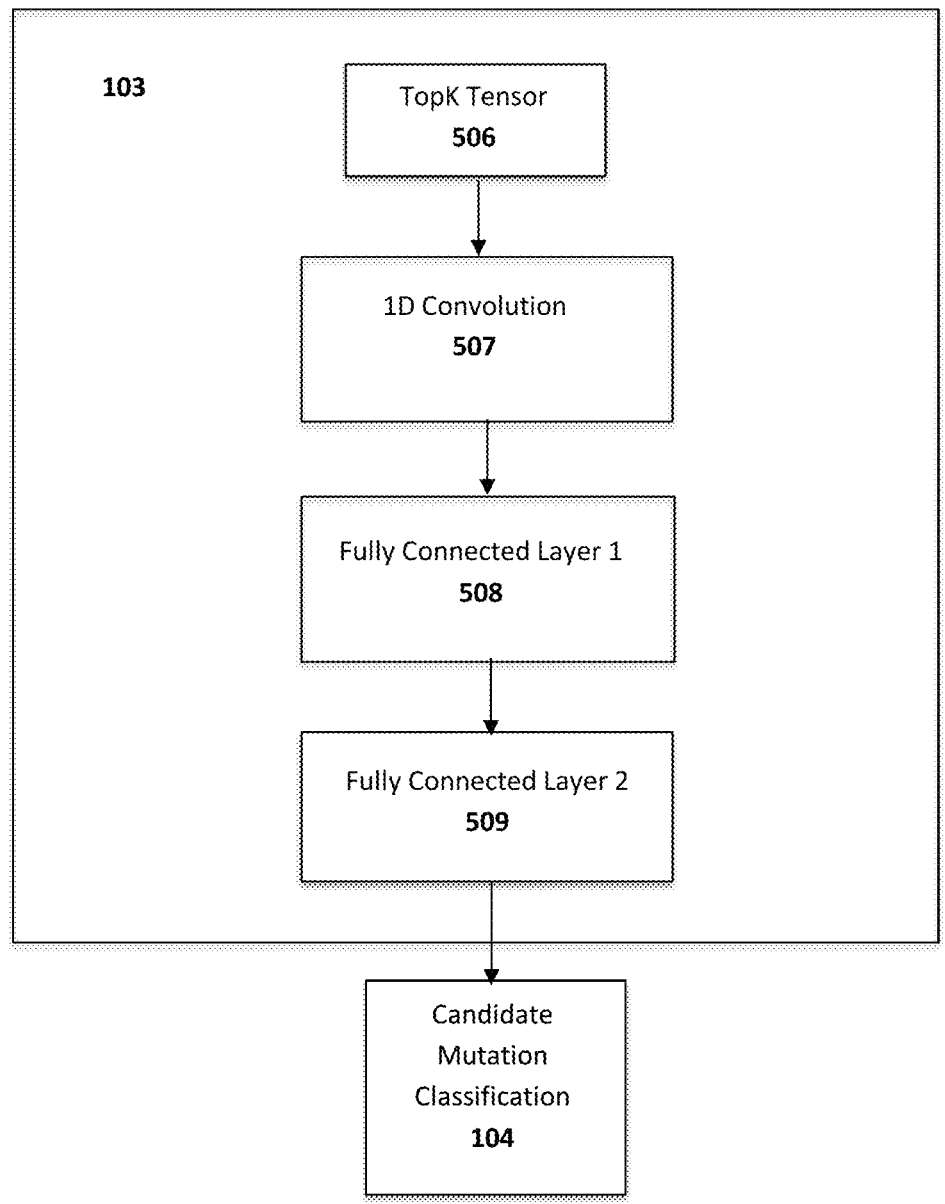

FIGS. 5A and 5B depict a block diagram illustrating an exemplary deep learning model architecture 103 useful for processing encoded information 102 representing candidate mutations and outputting a candidate mutation classification 104. As depicted in FIGS. 5A and 5B, in some embodiments of the present disclosure, the deep learning model comprises a sequence of two neural network modules, wherein the first neural network module comprising a plurality of parallel CNNs of differing kernel sizes whose output is combined into a single tensor representing extracted features of the encoded information, and a second neural network module comprising a 1D convolutional layer and fully connected layers capable of processing the tensor of the first module and outputting the classification of the candidate mutation 104.

FIG. 5A depicts an exemplary first neural network module wherein the input encoded data structure 102 is processed by a plurality of parallel 1D convolution layers 501, 502, and 503, having varying kernel sizes. As illustrated in FIG. 5A, there are three input 1D convolution layers of relative sizes X, 2X, and 4X. It is contemplated, however, that the difference in kernel sizes can vary in a range from about X to about 10X. In some embodiments, for example, the kernel sizes for three layers could be X, 1.5X-3X, and 4X-10X. In some embodiments, the plurality of CNNs can comprise kernel sizes described in terms of base pair (bp). For example, the plurality of three layers 501, 502, and 503, could have kernel sizes of 4 bp, 8 bp, and 16 bp, respectively. Also, as depicted in FIG. 5A, it is contemplated that that plurality of parallel 1D convolution layers 501, 502, and 503 of varying kernel sizes, can each comprise additional neural network layers that process in parallel. The output of each 1D convolution layers 501, 502, and 503 depicted in FIG. 5A is subsequently processed by ReLU and MaxPool layers 504. Generally, layers are of a size equal to or less than X, i.e., the kernel size of the smallest input convolution layer. Once again, as depicted in FIG. 5A, it is contemplated that each of the parallel ReLU and MaxPool layers can comprise additional parallel layers. As illustrated by the exemplary neural network of FIG. 5A, the parallel processed output of the convolution layers 501, 502, and 503 and subsequent ReLU and MaxPool layers 504 then is combined or concatenated into a single tensor 505.

As noted above, high-throughput sequencing datasets can potentially yield millions of candidate mutations, each at different genomic location and each having different characteristics of number of sequence reads, with different characteristics of mapping quality, and base quality associated with each read. The large number of and differing characteristics of each candidate mutation makes accurate and efficient candidate mutation classification using deep learning very difficult to achieve. It is a surprising technical effect and advantage of the deep learning model architecture illustrated in FIG. 5A is that processing encoded information in parallel using a plurality of CNNs of different kernel sizes that combine their output in a single tensor results in accurate and efficient candidate mutation classification. Moreover, the architecture provides accurate and efficient classification even when starting with suboptimal (e.g., low-coverage) sequencing datasets (e.g., average coverage less than 30X, less than 20X, less than 15X, or less than 10X).

Further, in some embodiments of the first neural network module of the present disclosure exemplified in FIG. 5A, concurrent with the concatenation process optional ranking scores also are generated (not shown). Optionally, these ranking scores are then used to generate a TopK-selected tensor 506 from tensor 505. Typically, the value of K for TopK selection useful in the methods of the present disclosure range from about 10 to about 100. The resulting TopK-selected tensor 506 output of the parallel plurality of CNNs has a significantly reduced size that can be processed more efficiently by the second neural network module illustrated in FIG. 5B. Indeed, it is a further surprising technical effect and advantage of the deep learning model architecture illustrated in FIG. 5A is that a reduced-size TopK-selected tensor 506, generated with K is from 10-100, can be processed to provide accurate and efficient candidate mutation classifications, even when starting with suboptimal (e.g., low-coverage) sequencing datasets (e.g., average coverage less than 30X, less than 20X, less than 15X, or less than 10X).

As illustrated in the exemplification of FIG. 5B, in some embodiments the deep learning model comprises a second neural network module comprising an initial 1D convolution layer 507 followed by at least two fully connected layers 508 and 509. This second neural network module is capable of accepting as input and processing the tensor output of the first module. The output of the final fully-connected layer of the second network is a classification of the candidate mutation 104. The output candidate mutation classification can include an output value, that based on whether it meets some predetermined threshold, confirms whether a true mutation has been observed at a specific location relative to a reference sequence. Additionally, the candidate mutation classification can provide further information, including the type of mutation, e.g., whether a SNP, insertion, deletion, etc.

Prior to using the deep learning model to classify candidate mutations, a training process is carried out in which the neural networks "learn" an optimal set of parameters (e.g., adjustable weighting factors) that result in the best fit of a training dataset (e.g., a suboptimal sequencing dataset) to a model reference dataset (e.g., a standard reference genome sequence). This learning process typically involves an iterative stochastic gradient descent-based minimization through the space of neural network adjustable weighting factors. The training process thus typically includes error calculation and then back-propagation of the error through the network to adjust the weighting parameters.

The training of a deep learning model to classify candidate mutations, as contemplated herein, can include both the more time-consuming initial training of model, and also include less time-consuming "transfer learning" training of a model that has previously been trained, but on a different dataset. For example, transfer learning can involve the further training of a neural network without re-learning the complete set of adjustable weighting parameters. Transfer learning may be carried out by training a neural network (e.g., CNN) that has already been trained with a suboptimal dataset using a new and/or slightly different type of dataset. For example, a deep learning model initially trained using candidate mutation information and sequencing data obtained from one type of NGS instrument could partially re-trained with information and data obtained from different type of NGS instrument. Thus, the learning from the initial training on the first type of NGS instruction would be transferred in the training of the neural network with model data from the second NGS instrument. Because it does not require starting over from scratch in adjusting the weighting parameters, the training process involved in transfer learning is greatly reduced. Accordingly, it is contemplated in the methods of the present disclosure for classifying candidate mutations from sequencing data that the method further comprises training the deep learning model. In some embodiments, this training corresponds to transfer learning using candidate mutation information and model sequencing data from a different type of sample, sequencing instruments, and/or candidate mutation calling software than was used in the original training of the deep learning model.

FIG. 6 illustrates an exemplary system and flow of operations for training and then using a trained deep learning model to classify candidate mutations. Suboptimal candidate mutation information 601 and model reference sequence data 602 are input into a system comprising a deep learning model training system 603. In order to train the deep learning model to classify mutations from suboptimal (e.g., low coverage) NGS data. Ideally, the model reference sequence 602 used in the training should be a reference sequence that provides the ground truth candidate mutation classification at every location. The model reference sequence 602 can thereby be used as the "ground truth" set for training the deep learning model. Typically, the model reference sequence is a fully-characterized sequence that has been determined using high-coverage sequencing dataset and confirmed by independently conducted experiments, such that it provides the true position and identity of every base in the sequence to an accepted degree of confidence.

In some embodiments, the model reference sequences useful in the training methods are obtained from high-quality (e.g., 30X or greater coverage) sequencing data wherein the true sequence at each location has been confirmed by repeated experiments. Such high-quality sequences useful as a model reference sequence for training can be prepared by carrying out high-quality NGS experiments and analysis on well-known samples. In some embodiments, the model reference sequence 602 can be a "gold-standard" genome sequence from a source such as the publicly available benchmark human genomes available from the "Genome in a Bottle Consortium" (available at: jimb.stanford.edu/giab) or the mouse genome from the "Mouse Genome Project" (available at: www.broadinstitute.org/mouse/mouse-genome-project).

The suboptimal candidate mutation information 601 can be obtained from sequencing datasets that are of a lower quality in some respect relative to the sequencing data used for the model reference sequence 602. For example, whereas a model reference sequence typically will be generated from a sequencing dataset obtained with an average of 30X or greater read sequence coverage across the full sequence, the suboptimal candidate mutation information 601 will be generated from a sequencing dataset obtained with an average of less than 30X, less than 20X, less than 15X, less than 12X, or even less than 10X sequence read coverage.

The ultimate accuracy of the trained deep learning model depends at least in part on the quality level of the model reference sequence 602. In some embodiments, for training, the model reference sequence 602 and the suboptimal candidate mutation information 601 are obtained from the same experiment or using the same experimental conditions. In some embodiments, the suboptimal candidate mutation information 601 can be prepared from the model reference sequence 602 sequencing data by excluding some portion of the read sequences thereby creating effectively a low-quality dataset. For example, by randomly excluding half of the sequence reads from a high-quality 30X coverage NGS dataset, it can be effectively down-graded to a suboptimal, 15X coverage dataset. Other methods known in the art for simulating low-quality data from high-quality dataset e.g., by introducing noise can also be used.

Generally, the suboptimal candidate information 601 is obtained from low-coverage sequencing datasets, whether experimentally obtained or simulated, using standard software tools for generating candidate mutations, such as GATK.

As shown in FIG. 6, the suboptimal candidate mutation information 601 is used together with the model reference sequence 602 as input to a deep learning model training system 603. The system 603 is configured for training the deep learning model to accurately classify candidate mutations obtained from suboptimal sequencing data. The process carried out by the deep learning model training system 603 comprises using the suboptimal candidate mutation information as input to the untrained deep learning model, obtaining the output candidate mutation classification from the untrained model, and determining the error of the classification relative to the ground truth candidate mutation classification of the model reference sequence. In some embodiments, the error determination is carried out using a loss function, or similar type of calculation that quantifies the error between the suboptimal candidate mutation classification and the true mutation classification that is known from the model reference sequence.

As noted above, training is an iterative process whereby the error of each iteration is used to adjust the model parameters, and when the error calculated at the end of an iteration drops below some threshold, the error is determined to be minimized and the deep learning model optimized. Accordingly, the training process comprises minimizing error in the classification of the suboptimal candidate mutation relative to a ground truth candidate mutation of the model reference sequence by adjusting parameters of the deep learning model.

In some embodiments, the minimizing the error is carried out through a stochastic gradient descent involving iterative adjustment of weighting parameters within the deep learning model that produces a trained deep learning model 103. A range of loss functions useful in training neural networks, such as CNNs, are known in the art and can be used in the candidate mutation classifying methods and systems of the present disclosure.

The computations and data manipulations carried out within the deep learning model for classifying candidate mutations from sequencing data are beyond the capabilities of a human. The training and use of the neural networks generally require high-performance, energy efficient computer processors and is often carried out using graphics processing units (GPUs) or farms of GPUs. Accordingly, in some embodiments, the present disclosure provides a computing device configured to apply the deep learning model in a process for candidate mutation classification from the vast quantities of digital data associated with a genome sequence.

FIG. 6 further illustrates a block diagram 600 of an exemplary computer-based system useful for training and using the trained neural network system to classify candidate mutations from obtained sequencing datasets in accordance with embodiments of the present disclosure. The primary computer-based elements include a training engine 610 and a classification engine 620. As described above, the training engine is configured to accept input of a suboptimal candidate mutation information 601 and input of a model reference sequence 602 and is connected to a memory device 630, which can comprise temporary memory and/or a persistent storage device. The training engine 610 carries out the computer-based instructions for configuring the neural networks of the deep learning model training system 603 based upon the training process. The deep learning model parameters during training can be stored in the memory device 630. The primary function of the training engine 610 in concert with the memory device 630 is to train and provide the final optimized deep learning model that can be accessed and used by the classification engine 620.

The computer-based implementation of the classification engine 620 is configured to accept input of the encoded information 102 representing candidate mutation information 101 and process it using the trained deep learning model 103 and output a candidate mutation classification 104. The input of the encoded information 102 and the output of the classifications 104 can be stored in the memory device 630.

It is contemplated that in some embodiments the classification engine 620 can provide further computer-based treatment prior to the input such as encoding the candidate mutation information 101 obtained from other software tools (e.g., GATK or SAMtools). It is also contemplated that the classification engine can provide further treatment of the output candidate mutation classifications such as reassembling the classified mutations to provide as output a sequence comprising the mutation, such as a full-length sequence based on the complete reference sequence.

The various computer-based elements illustrated in FIG. 6, and the functions attributed to them, are described generally for ease of understanding. One skilled in the art will recognize that one or more of the functions ascribed to the various elements may be performed by any one of the other elements, and/or by an element not shown in the figure. Furthermore, it is contemplated that the elements may be configured to perform a combination of the various functions described above as supported by the various embodiments described elsewhere herein. Accordingly, the description of a training engine 610, a classification engine 620, a and a memory device 630 are intended to include any suitable combination of computing devices, including servers, interfaces, systems, databases, agents, peers, engines, controllers, modules, or other types of computing devices operating individually or collectively to perform the functions ascribed to the various elements. Further, one skilled in the art will recognize that one or more of the functions of the system of FIG. 6 described herein may be performed within the context of a client-server relationship, such as by one or more servers, one or more client devices (e.g., one or more user devices) and/or by a combination of one or more servers and client devices.

Figure 7:
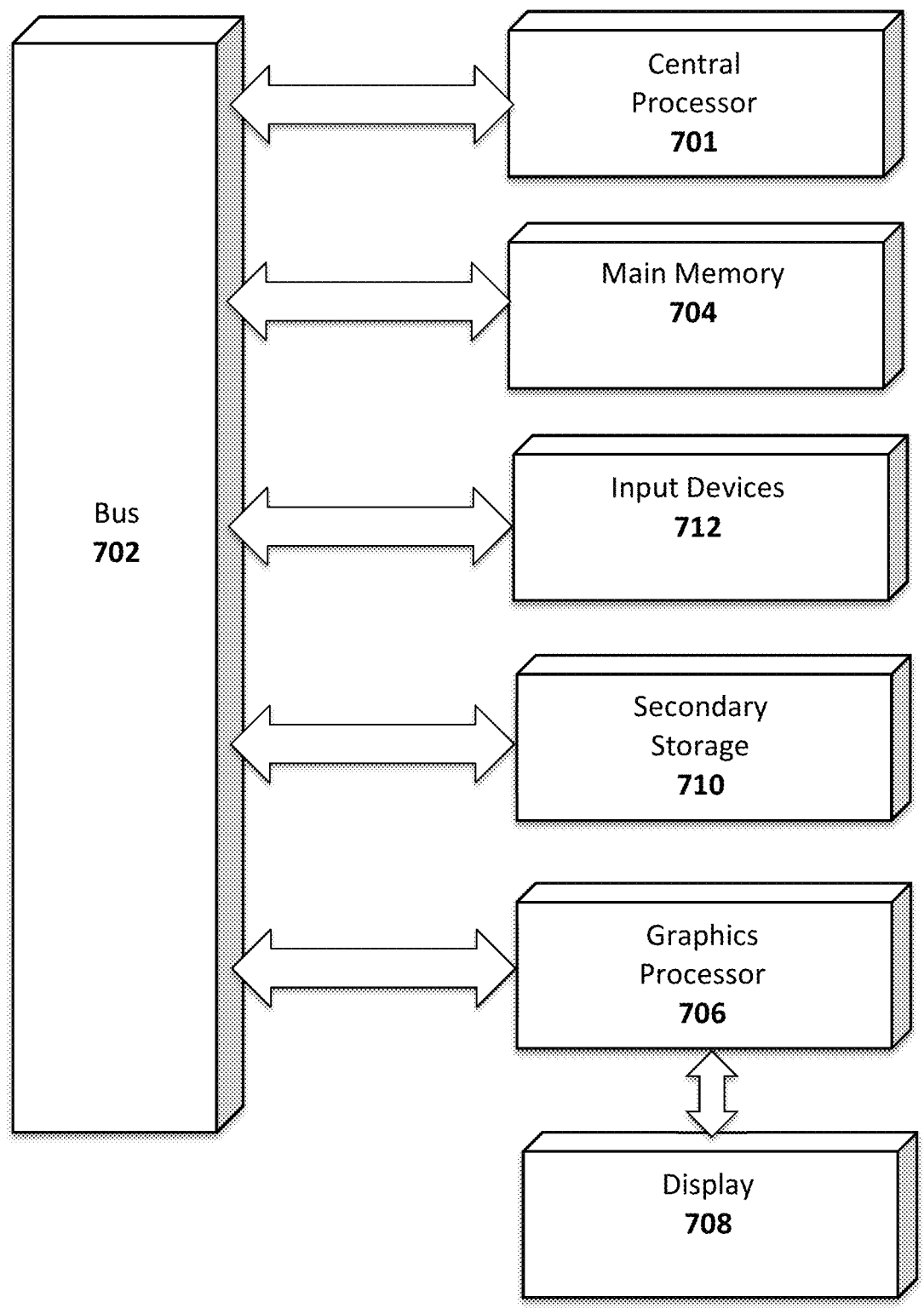
FIG. 7 depicts a system in which the processes, architecture, and/or functionality useful for classifying candidate mutations identified in sequencing data using a deep learning model in accordance with embodiments of the present disclosure may be implemented.

FIG. 7 depicts an exemplary system 700 in which the embodiments of the general candidate mutation classification process 100, the candidate mutation data encoding 200, the deep learning model architecture 400, and/or the training engine and classification engine functionalities 500 may be implemented. The system 700 includes at least one central processor 701 connected to a communication bus 702. The communication bus 702 may be implemented using any suitable protocol, such as PCI (Peripheral Component Interconnect), PCI-Express, AGP (Accelerated Graphics Port), HyperTransport, or any other bus or point-to-point communication protocol. The system 700 also includes a main memory 704. Control logic (software) and data are stored in the main memory 704 which may include random access memory (RAM). The system 700 also includes input devices 712, a graphics processor 706, and a display 708, such as a conventional CRT (cathode ray tube), LCD (liquid crystal display), LED (light emitting diode) display, and the like. User input may be received from the input devices 712, which can include, but is not limited to, keyboard, mouse, touchpad, microphone, and the like. In one embodiment, the graphics processor 706 may include a plurality of shader modules, a rasterization module, etc. Each of the foregoing modules may even be situated on a single semiconductor platform to form a graphics processing unit (GPU). As used herein, a single semiconductor platform may refer to a sole unitary semiconductor-based integrated circuit or chip, or to multi-chip modules with increased connectivity which simulate on-chip operation. The various modules may also be situated separately or in various combinations of semiconductor platforms per the desires of the user. The system 700 may also include a secondary storage 710, for example, a hard disk drive and/or a removable storage drive, representing a floppy disk drive, a magnetic tape drive, a compact disk drive, digital versatile disk (DVD) drive, recording device, universal serial bus (USB) flash memory.

Software instructions, computer programs, and/or computer control logic algorithms, may be stored in the system's main memory 704 and/or the secondary storage 710. Such software instructions, when executed, allow the system 700 to perform various functions. The main memory 704, secondary storage 710, and/or any other storage are examples of computer-readable media.

In one embodiment, the functionality and/or architecture of the various previous FIGS. 1-6 may be implemented in the context of the central processor 701, the graphics processor 706, an integrated circuit (not shown) that is capable of at least a portion of the capabilities of both the central processor 701 and the graphics processor 706, a chipset (i.e., a group of integrated circuits designed to work and sold as a unit for performing related functions, etc.), and/or any other integrated circuit.

In some embodiments, the functionality and/or architecture of FIGS. 1-6 may be implemented in the context of a general computer system, a circuit board system, an application-specific system, and/or any other desired system. For example, the system 700 may take the form of a desktop computer, laptop computer, server, workstation, embedded system, and/or any other type of logic. In some embodiments, the system 700 may take the form of various other devices including, but not limited to a personal digital assistant (PDA) device, a mobile phone device, a television, etc.

It is also contemplated, that in some embodiments, the system 700 may be coupled to a network (e.g., a telecommunications network, local area network (LAN), wireless network, wide area network (WAN) such as the internet, peer-to-peer network, cable network, or the like) for communication purposes.

In some embodiments, the methods and systems of classifying candidate mutations using deep learning as described in the present disclosure and exemplified by FIGS. 1-6, may be implemented, controlled, and/or otherwise utilized remotely via the internet, or other network system. For example, the system 700 could be hosted on one or more servers that could be accessed by remote users and used to classify candidate mutations from the users sequencing datasets. Accordingly, in some embodiments, users can upload their own sequencing datasets and/or candidate mutation information for classification using a fully trained version of the deep learning model 103 hosted on a server.

Additionally, in some embodiments users can also upload their own suboptimal sequencing datasets and/or suboptimal candidate mutations for further training of the deep learning model (e.g., reference learning) hosted on the remote servers. The user would then use the further trained deep learning model hosted on the servers to classify the candidate mutations generated by their own sequencing datasets. Typically, users would download the output mutation classifications for further use locally, however in some embodiments the hosted system for mutation classification could include other tools for analysis such as databases of model or suboptimal candidate mutation information, model reference sequences, and/or other data useful in various methods of sequence analysis described herein.

Generally, the computing devices useful with the deep learning-based mutation detection and classification processes and systems of the present disclosure can include any suitable combination of computing devices, including servers, interfaces, systems, databases, agents, peers, engines, controllers, modules, or other types of computing devices operating individually or collectively. At least one processor (e.g., GPU, CPU, ASIC, FPGA, DSP, x86, ARM, etc.) of the computing device is configured (or programmed) to execute software instructions stored on a computer readable tangible, non-transitory medium (e.g., hard drive, solid state drive, RAM, flash, ROM, etc.) and thereby carry out the processes involved in the methods of training and employing the deep learning model for classifying mutations.

The software instructions to configure or program the computing devices to provide the candidate mutation classification functionality can be prepared using standard programming tools. For example, the extraction and encoding of candidate mutation information from high-throughput sequencing data can be programmed using the specifications of the VCF and BAM file formats and software tools available online e.g., SAMtools repository at github.com/samtools. Deep learning model architecture and the neural network configurations can be programmed with the software tools such as Keras (v.2.1.3) and Tensorflow (v.1.4.0). Generally, the software instructions are embodied as a computer program product comprising a non-transitory, tangible computer readable medium storing the instructions that cause a processor of the computing device to execute the steps of the denoising processes disclosed herein.

Additionally, the methods of the present disclosure can be carried out using standard protocols and algorithms for data exchange between servers, systems, databases, or interfaces in implementing the processes. For example, data exchange used in implementing the methods and systems of the present disclosure can be conducted over a packet-switched network, a circuit-switched network, the internet, LAN, WAN, VPN (or other type of networks) using protocols based on HTTP, HTTPS, AES, public-private key exchanges, web service APIs, financial transaction protocols, or other electronic information exchange methods.

While the foregoing disclosure of the present invention has been described in some detail by way of example and illustration for purposes of clarity and understanding, this disclosure including the examples, descriptions, and embodiments described herein are intended to be exemplary, and should not be construed as limiting the present disclosure. It will be clear to one skilled in the art that various modifications or changes to the examples, descriptions, and embodiments described herein can be made and are to be included within the spirit and purview of this disclosure and the appended claims. Further, one of skill in the art will recognize a number of equivalent methods and procedures to those described herein. All such equivalents are to be understood to be within the scope of the present disclosure and are covered by the appended claims.

Additional embodiments of the invention are set forth in the following claims.

What is claimed is:

1. A method comprising:
   encoding information representing a candidate mutation, wherein the information comprises absolute location, reference sequence, number of reads (N), and read sequences, wherein the reference sequence and the read sequences are encoded as 2D Boolean matrices and the reference sequence is associated with each of the read sequences; and
   processing the encoded information with a deep learning model that jointly processes the reference sequence with each read sequence and classifies the candidate mutation.

2. The method of claim 1, wherein the encoding augments the reference sequence.

3. The method of claim 1, wherein the encoded information further comprises read mapping quality values and/or read base quality values.

4. The method of claim 1, wherein processing with a deep learning model comprises
   transforming the encoded information in parallel with a plurality of CNNs of different kernel sizes and combining the output into a tensor.

5. The method of claim 4, wherein combining the output comprises generating a ranking score and using it to generate TopK-selected tensor.

6. The method of claim 4, wherein the processing with a deep learning model further comprises
   transforming the tensor with a CNN comprising a 1D convolutional layer followed by a plurality of fully connected layers, wherein the final fully connected layer outputs the classification of the candidate mutation.

7. The method of claim 1, wherein the method further comprises training the deep learning model, wherein training comprises:
   encoding information representing a suboptimal candidate mutation, wherein the encoded information comprises absolute location, a model reference sequence, number of reads (N), and read sequences;
   processing the encoded information with a deep learning model that classifies the suboptimal candidate mutation; and
   minimizing error in the classification of the suboptimal candidate mutation relative to a ground truth candidate mutation of the model reference sequence by adjusting parameters of the deep learning model.

8. The method of claim 7, wherein the encoding associates the reference sequence with each read sequence, whereby the deep learning model jointly processes the reference sequence with each read sequence.

9. The method of claim 8, wherein processing with a deep learning model comprises
   transforming the encoded information in parallel with a plurality of CNNs of different kernel sizes and combining the output into a tensor.

10. The method of claim 9, wherein the processing with a deep learning model further comprises transforming the tensor with a CNN comprising a 1D convolutional layer followed by a plurality of fully connected layers, wherein the final fully connected layer outputs the classification of the suboptimal candidate mutation.

11. A system comprising a processor, a memory device, and a classification engine executable on the processor according to software instructions stored in the memory device, wherein the classification engine is configured to:
   encode information representing a candidate mutation, wherein the encoded information comprises absolute location, reference sequence, number of reads (N), and read sequences, wherein the reference sequence and the read sequences are encoded as 2D Boolean matrices and the reference sequence is associated with each of the read sequences; and
   process the encoded information with a deep learning model that jointly processes the reference sequence with each read sequence and classifies the candidate mutation.

12. The system of claim 11, wherein the encoded information further comprises read mapping quality values and/or read base quality values.

13. The system of claim 11, wherein the system further comprises a training engine executable on the processor according to software instructions stored in the memory device, wherein the training engine is configured to:
- encode information representing a suboptimal candidate mutation, wherein the encoded information comprises absolute location, a model reference sequence, number of reads (N), and read sequences, wherein the reference sequence and the read sequences are encoded as 2D Boolean matrices and the reference sequence is associated with each of the read sequences;
- process the encoded information with a deep learning model that jointly processes the reference sequence with each read sequence and classifies the suboptimal candidate mutation; and
- minimize error in the classification of the suboptimal candidate mutation relative to a ground truth candidate mutation of the model reference sequence by adjusting parameters of the deep learning model.

14. A non-transitory computer-readable medium comprising instructions for classifying candidate mutations that, when executed by a processor, cause the processor to perform one or more steps comprising:
- encoding information representing a candidate mutation, wherein the encoded information comprises absolute location, reference sequence, number of reads (N), and read sequences, wherein the reference sequence and the read sequences are encoded as 2D Boolean matrices and the reference sequence is associated with each of the read sequences; and
- processing the encoded information with a deep learning model that jointly processes the reference sequence with each read sequence and classifies the candidate mutation.

15. The non-transitory computer-readable medium of claim 14, wherein the medium further comprises instructions for training the deep learning model, wherein training comprises:
- encoding information representing a suboptimal candidate mutation, wherein the encoded information comprises absolute location, a model reference sequence, number of reads (N), and read sequences, wherein the reference sequence and the read sequences are encoded as 2D Boolean matrices and the reference sequence is associated with each of the read sequences;
- processing the encoded information with a deep learning model that jointly processes the reference sequence with each read sequence and classifies the suboptimal candidate mutation; and
- minimizing error in the classification of the suboptimal candidate mutation relative to a ground truth candidate mutation of the model reference sequence by adjusting parameters of the deep learning model.

* * * * *